United States Patent [19]

Sakamoto et al.

[11] Patent Number: 4,828,840
[45] Date of Patent: May 9, 1989

[54] SUSTAINED-RELEASE FORMULATION AND PRODUCTION THEREOF

[75] Inventors: Teruo Sakamoto, Osaka; Toyohiko Takeda, Hyogo; Yusuke Suzuki, Osaka; Kinzaburo Noda; Toshiro Fujii, both of Hyogo, all of Japan

[73] Assignee: Shionogi & Co., Ltd., Osaka, Japan

[21] Appl. No.: 66,512

[22] Filed: Jun. 26, 1987

[30] Foreign Application Priority Data

Jul. 17, 1986 [JP] Japan .................. 61-169255

[51] Int. Cl.⁴ .................. A61K 9/22; A61K 9/24; A61K 9/26
[52] U.S. Cl. .................. 424/474; 424/471; 424/472; 424/476; 424/478; 424/479; 424/480; 424/481; 424/482; 427/3
[58] Field of Search .................. 424/472, 473, 471, 474, 424/476, 478, 479, 480, 481, 482; 427/3

[56] References Cited

U.S. PATENT DOCUMENTS 4,454,108  6/1984  Iida et al. .................. 424/472
4,684,516  8/1987  Bhutani .................. 424/471 X Primary Examiner—Michael Lusignan
Attorney, Agent, or Firm—Wenderoth, Lind & Ponack

[57] ABSTRACT

Sustained-release formulations which can release a water-soluble active ingredient or ingredients at the zero-order over a long period of time, comprising:
 a. an inert core,
 b. a powder-coating layer containing a water-soluble active ingredient or ingredients,
 c. a powder-coating layer of practically water-repellent material, and
 d. a film-coating layer composed of practically pH-independent and water-insoluble film-coating material.

3 Claims, 2 Drawing Sheets

SUSTAINED-RELEASE FORMULATION AND PRODUCTION THEREOF

BACKGROUND OF THE INVENTION

1. Field of Invention

The present invention provides sustained-release formulations of a pharmacologically active ingredient or ingredients, especially of ones which have been hardly formulated because of their high solubility in water (hereinafter sometimes referred to as water-soluble active ingredients), and methods for preparing sustained-release formulations of them are also provided.

2. Prior Arts

A number of reports have been published on the technologies for effectively controlling dissolution and absorption of water-soluble pharmacologically active ingredients, especially of active ingredients which are very soluble in gastric or intestinal juice.

These technologies for sustainment of drugs may be classified generally into two types. One is achieved by forming matirix and the other is by film-coating.

For example, the sustained-release has been accomplished by granulating an active ingredient together with a hydrophobic substance to form matrices as disclosed in Japanese Patent Publication No. 60-56122. However, there is no disclosure on the release-control over four hours in the publication above.

In JPN Patent Application No. 61-1614, the sustained-release has been accomplished by making triple layers with three different types of pH-dependent film-coating materials. In the above process, however, troublesome coating steps are required and moreover a large amount of coating materials must be employed for the limited amount of the active component in order to achieve appropriate sustained-release. Moreover, the use of such a large amount of coating materials unfavourably decreases bio-availability of the active ingredients.

SUMMARY OF INVENTION

The present invention provides sustained-release formulations which can release the active ingredient or ingredients at the zero-order over a long period of time, comprising:
- a. an inert core,
- b. powder-coating layer containing a water-soluble active ingredient or ingredients,
- c. powder-coating layer of practically water-repellent material, and
- d. film-coating layer composed of practically pH-independent and water-insoluble film-coating material.

DESCRIPTION OF THE PREFERRED EMBODIMENT

Problem to be Resolved

Figure 1:
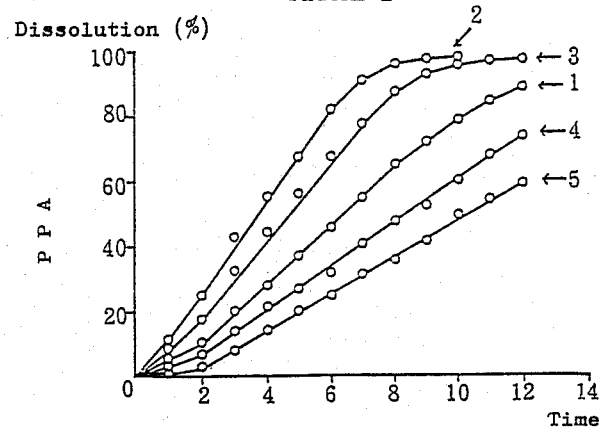
FIG. 1 shows the dissolution rate of PPA on the formulations of the present invention prepared in Examples 8 to 12. The numerals 1 to 5 in the Figure indicate the formulations of Examples 8 to 12, respectively.

In the methods of the sustained-release for formation of matrices or film-coating layers, the pattern of drug-releasing is very similar to the first-order-like one and the controllable duration of drug-release is limited to at most a few hours. In order to give a zero-order releasing pattern to the formulation, it is necessary to use a large amount of materials for forming matrices or film-coating layers, but this operation is accompanied with some defects such as decrease of bio-availability of active ingredients.

The present invention provides sustained-release formulations or means by which the active ingredients are released at a zero-order release, i.e. at a constant rate, over a period of 10 hours or longer. The present invention is very useful in preparing sustained-release formulations of such active ingredients as to be absorbed at a large area of the digestive organs, quickly but shortly act. According to the present invention, any formulations having desirable drug-release patterns, for example, rapidly acting but long-lasting formulations and the like can easily be prepared by means of the prior art techniques such as combination of slow-release preparations with rapid-release ones.

MEANS TO BE RESOLVED

The present inventors have accomplished this invention, based upon the findings that the zero-order release of said pharmacologically active ingredients over a long period of time is realized by providing a powder-coating layer containing said pharmacologically active ingredient onto the cores, and further making thereon a powder-coating layer of a practically water-repellent material, and then a film-coating layer of practically pH-independent and water-insoluble material.

In more detail, the present invention provides sustained-release formulations of a water-soluble active ingredient or ingredients comprising:
(a) inert cores,
(b) powder-coating layer containing a water-soluble active ingredient or ingredients,
(c) powder-coating layer of a practically water-repellent material, and
(d) film-coating layer composed of a practically pH-independent and water-insoluble film-coating material.

The sustained-release formulations of the present invention may be prepared in the following manners. The core materials are coated with powder which contains a water-soluble active ingredient or ingredients in the presence of a water-insoluble or very slightly soluble binding agent to give bare granules, and then said bare granules are coated with water-repellent powder so that the weight increases by about 10% to 80%, then dried, further coated with a practically pH-independent and water-insoluble film-coating material, if desired together with an enteric-coating material, a lubricant, a plasticizer, and the like, until the weight increases by about 20 to 60%, more preferably about 35 to 45%, and finally dried.

It is noted in this process that the drying steps should be operated at a lower temperature than the melting points of water-repellent materials. If it is done at a higher temperature than the melting point, said water-repellent material might be fused to result in interfering desirable release of said active ingredients.

The mechanism of the zero-order release concerning the thus prepared formulations of the present invention may be explained as follows. When the formulation orally administered reaches the stomach, moisture of the gastric juice permeates into the film-coating layer and then into the double powder-coating layers to gradually dissolve out the active ingredient from the surface of the inner powder-coating layer. The dissolved active ingredient is dispersed in the outer powder-coating layer and slowly released through the film-coating layer. At that time, the concentration of the active ingredient is kept constant in the outer powder-coating layer and, as a result, the zero-order release is maintained over a long period of time.

All the materials can be employed as the core material of this invention as long as they are pharmacologically inert and exhibit no interaction with the water-soluble pharmacologically active ingredients used. Saccharides or sugar alcohols such as sucrose, lactose, mannitol, xylitol and the like; various celluloses; various starches; and the like are exemplified. They may be employed in a form of crystals or singly or as a mixture in a form of granules or beads.

The term "the powder containing a water-soluble pharmacologically active ingredient" also indicates the active ingredient per se and, more preferably, a mixture of powder of the active ingredient with suitable excipients may be employed in order to improve operability in the coating process. The active ingredients are released at a high speed if a hydrophilic material is used as the excipient and, on the contrary, the releasing rate can be reduced if hydrophobic one is used. Further, the sustained-release formulations of slightly soluble active ingredients can be made by using hydrophilic materials.

Practically water-repellent materials include hardened glycerol fatty acid esters such as hardened castor oil, hardened beef tallow or the like; higher fatty acids such as stearic acid or the like; higher fatty acid metal salts such as magnesium stearate, calcium stearate, or the like; higher alcohols such as stearyl alcohol, cetanol, or the like; and waxes such as carnauba wax, beeswax, or the like. They may be employed singly or in a mixture of them, or two or more species of them may be applied to form multilayer coating.

Although the amounts of those materials to be used should not be limited imprudently because they vary with the sorts of the materials used, the density or size of the uncoated bare preparation, as well as the solubility of the active ingredient to be used, they may be used generally at an amount of about 10 to 80% by weight to the bare granules. The use of them at higher than the upper limitation reduces availability (capability of release) of the active ingredient, and at lower than the lower limitation, retardation is not sufficient.

The pH-independent and water-insoluble film-coating materials include ethylcellulose, copolymer of ethyl methacrylate and trimethylammoniumethyl chloride methacrylate (Eudragit® RS), shellac, highly polymerized polyvinyl alcohol, water-insoluble polyvinyl pyrrolidone, polyvinyl chloride, cellulose acetate, polyurethane, tetrafluoroethylene, polystyrene, polypropylene, lactic acid polymer, hydroxyethyl methacrylate, glycolic acid polymer, polyethylene terephtalate, polyethylene, polyamide, polyacrylonitrile, polycarboxylic acid, cyanoacrylic acid polymer, and the like. Especially, ethylcellulose and copolymer of ethyl methacrylate and trimethylammoniumethyl chloride methacrylate may preferably be employed.

The film-coating materials may be employed together with suitable additives, if necessary. The additive means enteric coating materials, water-soluble coating materials, lubricants, plasticizers, or the like. The enteric coating materials include hydroxypropylmethylcellulose phthalate (HPMCP), hydroxypropylmethylcellulose acetate succinate (HPMC-AS), copolymer of methacrylic acid and methyl methacrylate, cellulose acetate phthalate (CAP), and the like. The water-soluble coating materials include methylcellulose (MC), hydroxypropylcellulose (HPC), polyvinyl pyrrolidone (PVP), polyvinyl alcohol (PVA), gelatin, hydroxypropylmethylcellulose (HPMC), polycarboxylic acid (Carbopol®), starches, sodium alginate, and the like. The lubricants include talc, stearic acid, magnesium stearate, and like. The plasticizers include triacetin and the like.

The amounts of film-coating materials to be used should not be limited because they vary with the sort or the amount of additives. Generally, the materials may be employed at an amount of about 20 to 60%, preferably about 35–45% to the bare granules. Availability of the active ingredient decreases rapidly when the coating material is used over the upper limitation, and retardation also decreases rapidly at below the lower limitation.

EFFECTS

In the sustained-release formulations of the present invention, the releasing-rate of the active ingredient is exactly controllable depending upon powder-coating layer of practically water-repellent materials and, as a result, this minimizes the necessary amount of film-coating materials. Therefore, almost 100% of the active ingredient can be released from the formulation at a constant rate, even if it is so designed as to act over 10 hours.

Because the sustained-release formulations of the present invention are pH-independent, they are expected to have the same releasing property in aged persons or persons with hypochlorhydria or anacidity as in the healthy persons.

Many sustained-release formulations which consist essentially of hardened oils, triglycerol, and the like have been shown in the prior arts, but they have such a disadvantage as to be sensitive to digestive enzymes including lipase, esterase, and the like or bile acid. On the other hand, the formulations of the present invention are not influenced by such things.

The present invention is explained in more detail by the following Examples and Experiments, which are not intended to limit the scope of the present invention.

EXAMPLE (General Procedures for Sustained-release Formulations)

In the presence of additives, cores are coated with powder containing an active ingredient or ingredients to give bare preparations, each of which has a drug layer. The bare preparations are, in the presence of additives, powder-coated with water-repellent materials and then dried at 60° C. for an hour with forced aeration. Thus prepared granules are coated with film-coating materials by a pan-coating method and then dried at 80° C. for 20 minutes with forced aeration to give spherical sustained-granules.

REFERENCE EXAMPLE 1

(Preparation of Cores)

Mixed powder of 2500 g of D-mannitol, 200 g of crystalline cellulose, and 650 g of corn starch were triturated through a 80-mesh screen, and granulated, in the presence of 2% aqueous solution of methylcellulose as a binder, by a wetting method with Supermixer (made by Kawata Seisakusho) to give four different sizes of granules, i.e. mean particle sizes about 230 $\mu$m, about 320 $\mu$m, about 500 $\mu$m, and about 710 $\mu$m.

REFERENCE EXAMPLE 2

(Preparation of Rapid-release Formulation)

200 g Of the granules about 320 $\mu$m in mean particle size which were prepared in Reference Example 1 was coated with mixed powder of 250 g of phenylpropanolamine chloride, 1 g of belladonna total alkaloids and 300 g of D-mannitol, which was in advance triturated through a 80-mesh screen by using Supermixer, while 500 g of a 2% aqueous solution of methylcellulose 25 cps as a binder was sprayed thereon at a rate of 12 g per minute. The granules were dried at 60° C. for an hour with forced aeration to give spherical rapid-release granules of about 480 $\mu$m in mean particle size. The resulting granules contain 332 mg of phenylpropanolamine chloride and 1.3 mg of belladonna total alkaloids per gram.

This formulation is used as a long-acting formulation by combining with a sustained-release formulation prepared in the following Examples.

REFERENCE EXAMPLE 3

(Preparation of Rapid-release Formulation)

According to the manner shown in Reference Example 2, a rapid-release formulation was prepared with using 200 g of the granules of about 320 $\mu$m in mean particle size. The granules contain 333 mg of phenylpropanolamine chloride per gram and are about 480 $\mu$m in mean particle size.

This formulation is used as a long-acting formulation by combining with a sustained-release formulation prepared in the following Examples.

REFERENCE EXAMPLE 4

(Preparation of Long-acting Formulation)

Each gelatin hard capsule (size No. 2) was filled with 174 mg of sustained-release granules prepared in Example 18 and 45 mg of rapid-release granules prepared in Reference Example 2 to give a long-acting formulation, which contains 70 mg of phenylpropanolamine chloride and 0.27 mg of belladonna total alkaloids per capsule.

REFERENCE EXAMPLE 5

(Preparation of Long-acting Formulation)

Each gelatin hard capsule (size No. 2) was filled with 158 mg of sustained-release granules prepared in Example 8 and 60 mg of rapid-release granules prepared in Reference Example 2 to give a long-acting formulation, which contains 70 mg of phenylpropanolamine chloride per capsule.

REFERENCE EXAMPLE 6

(Preparation of Long-acting Formulation)

Each gelatin hard capsule (size No. 2) was filled with 174 mg of sustained-release granules prepared in Example 8 and 45 mg of rapid-release granules prepared in Reference Example 2 to give a long-acting formulation, which contains 70 mg of phenylpropanolamine chloride per capsule.

According to the General Procedures for Sustained-release Formulations, following formulations were prepared.

EXAMPLE 1

(Preparation of Bare Granules)

Using 200 g of granules (about 320 $\mu$m in mean particle size) as cores which were prepared in Reference Example 1, a mixed powder of 400 g of phenylpropanolamine chloride with 70 g of hardened castor oil which was screened through 80-mesh was powder-coated onto the core granules by using Supermixer, while 500 g of a 2% ethanol solution of ethylcellulose 100 cps as a binder was sprayed thereon at a rate of 16 g per minute, to form a layer of the active ingredient on said granules.

EXAMPLE 2

(Preparation of Bare Granules)

In the same manner as in Example 1, a mixed powder of 40 g of d-chlorpheniramine maleate, 250 g of D-manitol, 80 g of hardened castor oil, and 30 g of corn starch was coated onto the granules (200 g) of about 320 $\mu$m in mean particle size to give a layer of the active ingredient thereon.

EXAMPLE 3

(Preparation of Bare Granules)

Bare granules were prepared in the same manner as in Example 2 except that the granules (200 g) of about 230 $\mu$m in mean particle size were used.

EXAMPLE 4

(Preparation of Bare Granules)

Bare granules were prepared in the same manner as in Example 2 except that the granules (200 g) of about 500 $\mu$m in mean particle size were used.

EXAMPLE 5

(Preparation of Bare Granules)

Bare granules were prepared in the same manner as in Example 2 except that the granules (200 g) of about 710 $\mu$m in mean particle size were used.

EXAMPLE 6

(Preparation of Bare Granules)

In the same manner as in Example 1, a mixed powder of 1.5 g of belladonna total alkaloids, 400 g of sucrose, and 68.5 g of hardened castor oil was coated onto the granules (200 g) of about 320 μm in mean particle size to give a layer of the active ingredient thereon.

EXAMPLE 7

(Preparation of Bare Granules)

In the same manner as in Example 1, a mixed powder of 400 g of phenylpropanolamine chloride, 1.5 g of belladonna total alkaloids, and 68.5 g of hardened castor oil was coated onto the granules (200 g) about 320 μm in mean particle size to give a layer of the active ingredients thereon.

EXAMPLE 8

Onto the whole amount of the bare granules prepared in Example 1 were coated a mixed powder of 240 g of hardened castor oil with 80 g of magnesium stearate by Supermixer, while 250 g of a 5% ethanol solution of ethylcellulose 100 cps as a binder was sprayed thereon at a rate of 8 g per minute. The granules were dried at 60° C. for an hour with forced aeration and, as a result, they become to have a powder-coating layer thereon at about 46% by weight of the bare granules.

A solution of 174 g of ethylcellulose, 8.7 g of methacrylic acid and methyl methacrylate copolymer, and 90 g of talc in a mixture of ethanol (1250 g) with dichloromethane (3150 g) was coated onto the granules by a pan-coating method to give film-coated granules, which were dried at 80° C. for 20 minutes with forced aeration. They are spherical sustained-release granules of about 500 μm in mean particle size, which have a film-coating layer in each particle at about 40% by weight of the bare granules. The resulting granules contain 316 mg of phenylpropanolamine chloride per gram.

In the following Examples and Experiments, the amount of powder-coating or of film-coating is shown as weight % of the bare granules used therefor.

EXAMPLES 9 TO 12

Whole amount of the bare granules prepared in Example 1 were applied to each Example to give the following spherical granules of about 500 μm in mean particle size, which have different amounts of powder-coating layers.

Prescription of the powder-coating or film-coating is the same as shown in Example 8.

TABLE 1

| Example Number | Amount of Powder-coating | Amount of Film-coating | Amount of PPA in each gram |
| --- | --- | --- | --- |
| 9 | 24% | 40% | 358 mg |
| 10 | 35% | 40% | 336 mg |
| 11 | 55% | 40% | 301 mg |
| 12 | 65% | 40% | 287 mg |

Note:
PPA stands for phenylpropanolamine chloride.

EXAMPLE 13

Onto the whole amount of the bare granules prepared in Example 2 were coated a mixed powder of 200 g of hardened castor oil with 100 g of hardened beef tallow by Supermixer, while 125 g of a 10% ethanol solution of ethylcellulose 10 cps (binder) was sprayed thereon at a rate of 8 g per minute. The granules were dried at 60° C. for an hour with forced aeration and, as a result, they become to have a powder-coating layer thereon at about 43% by weight of the bare granules.

A film-coating dispersion of 174 g of ethylcellulose, 20 g of hydroxypropylmethylcellulose phthalate-55 (HPMCP-55), and 100 g of stearic acid in a mixture of ethanol (1200 g) with dichloromethane (3800 g) was sprayed onto the resulting granules at the spraying-rate of 35 g/min. The film-coated granules were dried at 80° C. for 30 minutes with forced aeration to give spherical sustained-release granules of about 500 μm in mean particle size, each particle of which has a film-coating layer at about 43% by weight of the bare granules. The granules contain 31.6 mg of d-chlorpheniramine maleate per gram.

EXAMPLE 14

Sustained-release granules were prepared in the same manner as in Example 13. Powder-coating layer (43%) and then film-coating layer (43%) whose prescriptions are the same as in Example 13 were formed on all the bare granules prepared in Example 3 to give spherical sustained-release granules of 320 μm in mean particle size. The granules contain 31.6 mg of d-chlorpheniramine maleate per gram.

EXAMPLE 15

Spherical sustained-release granules of 750 μm in mean particle size were obtained in the same manner as in Example 14 except the bare granules prepared in Example 4 were used. The granules contain 31.6 mg of d-chlorpheniramine maleate per gram.

EXAMPLE 16

Spherical sustained-release granules of 1500 μm in mean particle size were obtained in the same manner as in Example 14 except the bare granules prepared in Example 5 were used. The granules contain 31.6 mg of d-chlorpheniramine maleate per gram.

EXAMPLE 17

Spherical sustained-release granules of 500 μm in mean particle size were obtained in the same manner as in Example 8 except the bare granules prepared in Example 6 were used. The granules contain 1.19 mg of belladonna total alkaloids per gram.

EXAMPLE 18

Spherical sustained-release granules of 500 μm in mean particle size were obtained in the same manner as in Example 8 except the bare granules prepared in Example 7 were used. The granules contain 316 mg of phenylpropanolamine chloride and 1.19 mg of belladonna total alkaloids per gram.

EXPERIMENT

EXPERIMENT 1

Dissolution tests (paddle method) were practiced on the sustained-release granules prepared in Examples 8 to 12 in the second fluid (artificial intestinal juice) shown in JPN Pharmacopoeia X. The granules tested in each group contain 50 mg of PPA. Every formulation showed a preferable zero-order releasing pattern (FIG. 1).

EXPERIMENT 2

Figure 2:
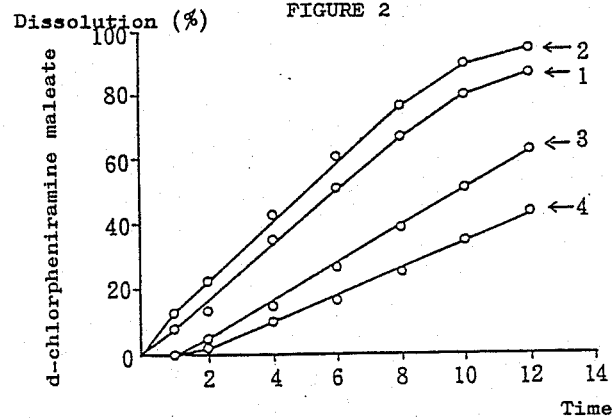
FIG. 2 shows the dissolution rate of d-chlorpheniramine maleate on the formulations of the present invention prepared in Examples 13 to 16. The numerals 1 to 4 in the Figure indicate the formulations of Examples 13 to 16, respectively.

Same dissolution tests (paddle method) as in Experiment 1 were practiced on sustained-release granules prepared in Examples 13 to 16. Granules containing 5 mg of d-chlorpheniramine maleate were employed for each test. The results show the fact that larger the mean partile size, smaller the dissolution rate and that the granules showed preferable zero-order releasing patterns independently of the sizes of the granules (FIG. 2).

EXPERIMENT 3

Figure 3:
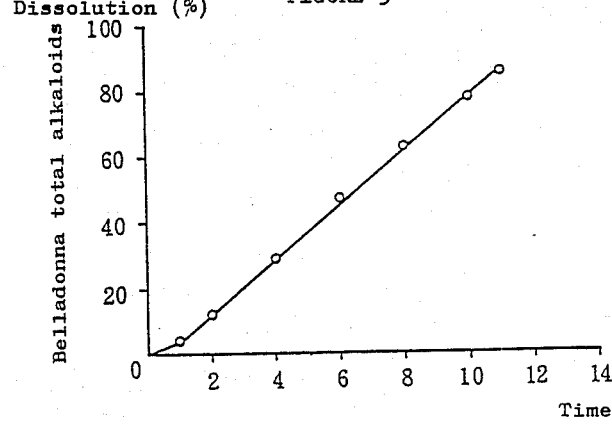
FIG. 3 shows the dissolution rate of belladonna total alkaloids on the formulation of the present invention prepared in Examples 17.

Same dissolution test (paddle method) as in Experiment 1 was practiced on sustained-release granules prepared in Examples 17. Granules containing 0.3 mg of belladonna total alkaloids were employed for each test. The granules showed preferable zero-order releasing patterns even if the active ingredient therein would be as littls as 0.1 weight % to the granules (FIG. 3).

EXPERIMENT 4

Figure 4:
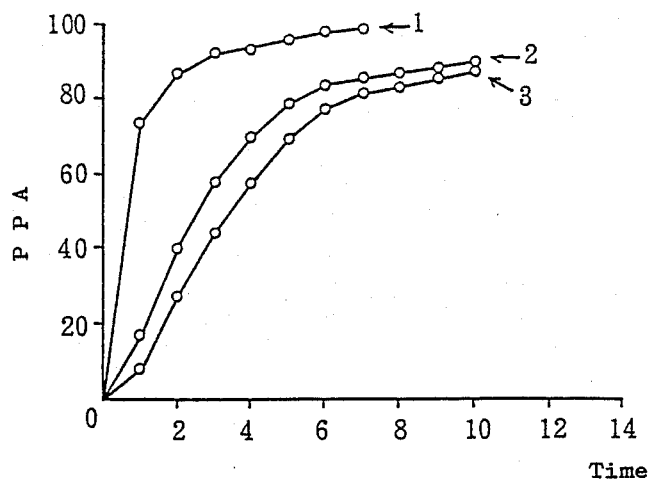
FIG. 4 shows the dissolution rate of PPA on the formulation of the prior art prepared in Experiment 4. The numerals 1 to 3 in the Figure indicate the Reference Formulations No. 1 to 3, respectively.

The formulations of the present invention were compared with those of the prior arts which were prepared by the following manner (FIG. 4).

(Reference Formulations 1 to 3 Production thereof)

Same film-coating solution as used in Example 8 was sprayed onto the granules of Example 2 to give three kinds of sustained-release granules which have different amounts of coating-layers but are the same in size (mean particle size is 480 μm). These formulations have no powder-coating layers.

TABLE 2

| Reference Formulations (Prior Arts) | Amount of Film Coating (%) | Amount of PPA in 1 g of the Granules |
|---|---|---|
| 1 | 34.4 | 438 mg |
| 2 | 37.3 | 428 mg |
| 3 | 44.8 | 406 mg |

From the results above, it can be understood that formulations of the prior arts show the first-order releasing patterns and the dissolution rate cannot be controlled by changing amounts of film-coating layers.

EXPERIMENT 5

Figure 5:
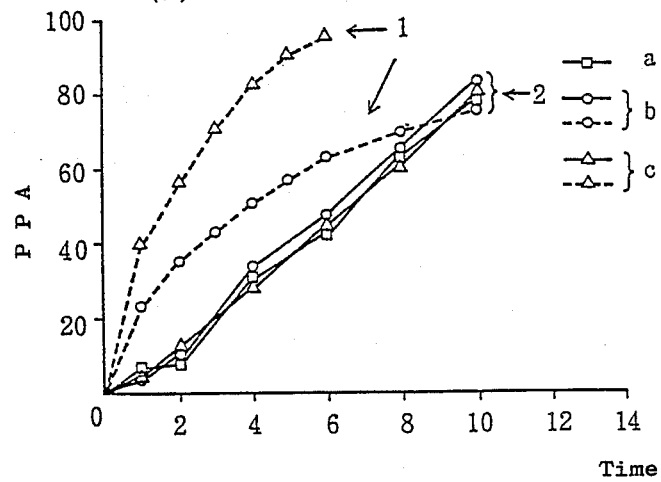
FIG. 5 shows the dissolution rate of PPA in the three kinds of test fluids (a, b, and c) listed in Experiment 5 on the present formulation of Example 8 and on the Reference Formulation No. 2 prepared in Experiment 4. In the figure, the numerals 1 and 2 indicate Reference Formulation No. 2 and the formulation of the present invention prepared in Example 8, respectively.

In order to study pH-dependency of the formulations of the present invention and their influence by gastric enzymes, dissolution test was practiced by using the following fluids (FIG. 5).

| Test Fluids |  |
|---|---|
| a. the first fluid shown in JPN Pharmacopoeia X, | |
| b. the second fluid shown in JPN Pharmacopoeia X, and | |
| c. mixture consisting of the following: | |
| the second fluid | 900 ml |
| pancreatin | 0.7 g |
| lipase | 0.7 g |
| gall powder | 2.0 g |
| Tested Formulations | |
| The present invention | Example 8 |
| Reference | Reference Formulation No. 2 |

Granules containing 50 mg of PPA were employed for the test.

The formulation of the present invention showed a preferable zero-order releasing pattern independently of change in pH value and of presence or absence of gastric enzymes. On the other hand, the dissolution rate on the reference formulation was significantly influenced by the gastric enzymes.

Preferable blood concentration-time curves were seen in a trial where the sustained-release formulation prepared in Reference Example 5 or 6 was administered to several healthy adults. It was, therefore, confirmed that the formulations of the present invention would give clinically preferable drug-releasing patterns.

What is claimed is:

1. A sustained-release formulation of a water-soluble active ingredient or ingredients comprising:
   (a) an inert core,
   (b) a powder-coating layer containing an effective amount of a water-soluble active ingredient or effective amounts of said ingredients surrounding the core (a),
   (c) a powder-coating layer of a practically water-repellent material surrounding the layer (b), and
   (d) a film-coating layer composed of a practically pH-independent and water-insoluble film-coating material surrounding the layer (c),
   wherein the powder-coating layer (c) is present in an amount of about 10% to 80% by weight based upon the amount of bare granules in layers (a) plus (b), and the film-coating layer (d) is present in an amount of about 20% to 60% by weight based on the weight of said bare granules.

2. A sustained release formulation according to claim 1 in which the inert core comprises a material selected from the group consisting of sucrose, lactose, manitol, xylitol and starch; the water-repellant material in coating layer (c) is selected from the group consisting of hardened castor oil, hardened beef tallow, stearic acid, magnesium stearate, calcium stearate, stearyl alcohol, cetanol, carnauba wax and beeswax, and the pH-independent and water-insoluble film coating material in coating layer (d) is selected from the group consisting of ethylcellulose, a copolymer of ethyl meythacrylate and trimethylammoniumethyl chloride methylacrylate, shellac, a highly polymerized polyvinyl alcohol, a water-insoluble polyvinyl pyrrolidone, polyvinyl chloride, cellulose acetate, polyurethane, tetrafluoroethylene, polystyrene, polypropylene, a lactic acid polymer, hydroxyethyl methacrylate, a glycol acid polymer, polyethylene terephtalate, polyethylene, polyamide, polyacrylonitrile, polycarboxylic acid and a cyanoacrylic acid polymer.

3. A process for production of sustained-release formulations of a water-soluble active ingredient or ingredients comprising coating powder which contains an effective amount or effective amounts of a water-soluble active ingredient or ingredients in the presence of a water-insoluble or very slightly soluble binding agent onto core materials to make bare granules, further coating a powder of a water-repellent material onto said bare granules at a rate of about 10 to 80% by weight to said bare granules, and then after a drying step, coating a practically pH-independent and water-insoluble film-coating material thereon, if desired, together with an enteric-coating material, a lubricant, a plasticizer, and the like, at a rate of about 20 to 60%, more preferably at about 35 to 45% by weight to said bare granules, and then drying.

* * * * *